United States Patent
Jones et al.

(10) Patent No.: US 11,398,112 B2
(45) Date of Patent: Jul. 26, 2022

(54) PULSE WAVE DETECTION DEVICE, VEHICLE DEVICE, AND PULSE WAVE DETECTION PROGRAM

(71) Applicant: AISIN CORPORATION, Kariya (JP)

(72) Inventors: Michael Jones, Tokyo (JP); Atsushi Sato, Tokyo (JP)

(73) Assignee: AISIN CORPORATION, Kariya (JP)

( * ) Notice: Subject to any disclaimer, the term of this patent is extended or adjusted under 35 U.S.C. 154(b) by 142 days.

(21) Appl. No.: 16/652,447

(22) PCT Filed: Sep. 5, 2019

(86) PCT No.: PCT/JP2019/034946
§ 371 (c)(1),
(2) Date: Mar. 31, 2020

(87) PCT Pub. No.: WO2020/050357
PCT Pub. Date: Mar. 12, 2020

(65) Prior Publication Data
US 2020/0285832 A1 Sep. 10, 2020

(30) Foreign Application Priority Data
Sep. 7, 2018 (JP) .............................. JP2018-167724

(51) Int. Cl.
*G06V 40/16* (2022.01)
*B60R 11/04* (2006.01)
*G06V 40/10* (2022.01)

(52) U.S. Cl.
CPC ............ *G06V 40/166* (2022.01); *B60R 11/04* (2013.01); *G06V 40/10* (2022.01); *G06V 40/169* (2022.01);
(Continued)

(58) Field of Classification Search
CPC ........... G06K 9/00255; G06K 9/00275; G06K 9/00885; G06K 2009/00939;
(Continued)

(56) References Cited

U.S. PATENT DOCUMENTS 10,595,732 B2 * 3/2020 Jones ..................... G06T 1/0007
2006/0102843 A1 * 5/2006 Bazakos ............ G06K 9/00255
250/339.05

(Continued)

FOREIGN PATENT DOCUMENTS

CN 107370955 A 11/2017
JP 2011-130996 A 7/2011
(Continued)

OTHER PUBLICATIONS

Daniel Teichmann et al. "Non-Contact Monitoring Techniques—Principles and Applications". Proc. IEEE Eng. Med. Biol. Soc. 34th Ann. Int. Conf., San Diego, CA, USA, 2012, pp. 1302-1305.
(Continued)

*Primary Examiner* — Nimesh Patel
(74) *Attorney, Agent, or Firm* — Oliff PLC

(57) ABSTRACT

A pulse wave detection device detects the face from a frame image and corrects the brightness of the face in accordance with the size of the face surface to appropriately detect a pulse wave even if brightness is changed due to movement of a subject with respect to lighting. The brightness of the face depends on the distance between the lighting and the face, and this is equal to indirect measurement of the distance from the lighting to the face using the size of the face. As described above, a pulse wave detecting device estimates/measures a pulse rate of the subject from a brightness signal after intensity of the brightness of the face photographed on the frame image is corrected using the size of the face, by using the correlation between the size of the
(Continued)

face of the subject on the frame image and the brightness of the face.

10 Claims, 10 Drawing Sheets

(52) U.S. Cl.
CPC ...... *B60R 2300/8006* (2013.01); *G06V 40/15* (2022.01); *G06V 2201/03* (2022.01)

(58) Field of Classification Search
CPC .......... G06K 2209/05; G06K 9/00268; G06K 9/4661; G06K 9/00046; G06K 9/0004; G06K 9/00906; G06K 2209/01; G06K 9/00087; G06K 9/00107; G06K 9/0012; G06K 9/2036; G06K 9/209; G06K 9/22; G06K 9/46; G06K 9/00201; G06K 9/6288; G06K 9/629; G06K 9/00335; G06K 9/00355; G06K 9/00114; G06K 9/00228; G06K 9/00234; G06K 9/00302; G06K 9/00362; G06K 9/3233; G06K 9/00765; G06K 9/00771; G06K 9/00899; B60R 11/04; B60R 2300/8006; A61B 5/0077; A61B 5/02108; H04L 63/1483; H04L 63/1491; G02F 1/13338; G02F 1/133504; G02F 1/133606; G02F 1/133607; G02F 1/1335; G02B 6/00; G02B 6/0051; G02B 6/0055; G02B 6/0076; G06F 16/95; G06F 21/31; G06F 21/445; G06F 21/552; G06F 21/577; G06F 21/6218; G06F 2221/2101; G06F 2221/2115; G06F 2221/2119; G06F 3/017; G06F 21/32; G06F 1/3206; G06F 21/629; G06F 21/88; G01J 2005/0077; G01J 2005/0085; G01J 5/12; G01J 5/0025; G01S 7/415; G01S 13/66; G01S 13/867; G01S 7/41; G01S 13/56; G01S 13/86; G01S 13/888; G01S 13/931; G01S 19/42; G01S 13/02; G01S 13/89; G01S 15/06; G01S 15/10; G01S 15/89; G01S 19/17; G01S 5/02; G01S 2013/462; G01S 7/40; G01S 7/411; G06T 2207/30076; G06T 7/0012; G06T 2207/10016; G06T 7/75; G06T 2207/20216; G06T 2207/30088; G06T 7/0016; G06T 2207/30201; G06T 7/73; G06T 2207/20021; G06T 2207/20056; G06T 7/0014; G06T 7/11; G06T 7/20; G06T 7/254; G06T 7/90; G06V 40/166; G06V 40/10; G06V 40/169; G06V 40/15; G06V 2201/03; G06V 10/60; G06V 40/168

See application file for complete search history.

(56) References Cited

U.S. PATENT DOCUMENTS

| | | | | |
|---|---|---|---|---|
| 2007/0025722 | A1* | 2/2007 | Matsugu | ............... G06T 7/97 396/263 |
| 2009/0087041 | A1 | 4/2009 | Hasebe et al. | |
| 2015/0379362 | A1* | 12/2015 | Calmes | ............... G06T 7/20 348/136 |
| 2016/0117544 | A1* | 4/2016 | Hoyos | ............ G06K 9/00604 348/78 |
| 2016/0317041 | A1* | 11/2016 | Porges | ............... A61B 5/0037 |
| 2016/0371555 | A1* | 12/2016 | Derakhshani | ...... G06K 9/00228 |
| 2017/0112382 | A1* | 4/2017 | Nakata | ............... A61B 5/0245 |
| 2017/0281050 | A1 | 10/2017 | Noguchi et al. | |
| 2018/0085010 | A1 | 3/2018 | Jones et al. | |
| 2018/0202823 | A1 | 7/2018 | Maekawa et al. | |
| 2019/0354746 | A1* | 11/2019 | Zhang | ............ G06K 9/00268 |

FOREIGN PATENT DOCUMENTS

| | | |
|---|---|---|
| JP | 2014-161355 A | 9/2014 |
| JP | 2014-198201 A | 10/2014 |
| JP | 2016-193021 A | 11/2016 |
| JP | 2016-193022 A | 11/2016 |
| JP | 2018-114266 A | 7/2018 |
| WO | 2016-104538 A1 | 6/2016 |

OTHER PUBLICATIONS

Nov. 19, 2019 International Search Report issued in International Patent Application No. PCT/JP2019/034946.
Mar. 9, 2021 International Preliminary Report on Patentability issued in International Patent Application No. PCT/JP2019/034946.
May 11, 2022 Extended European Search Report issued in European Patent Application No. 19857297.6.

* cited by examiner

FIG.6
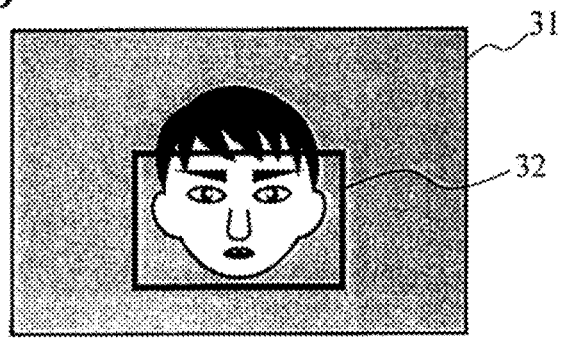
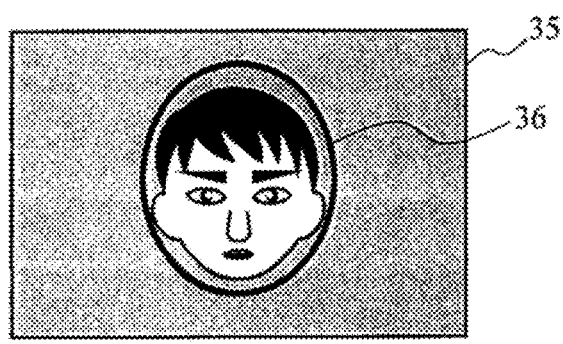
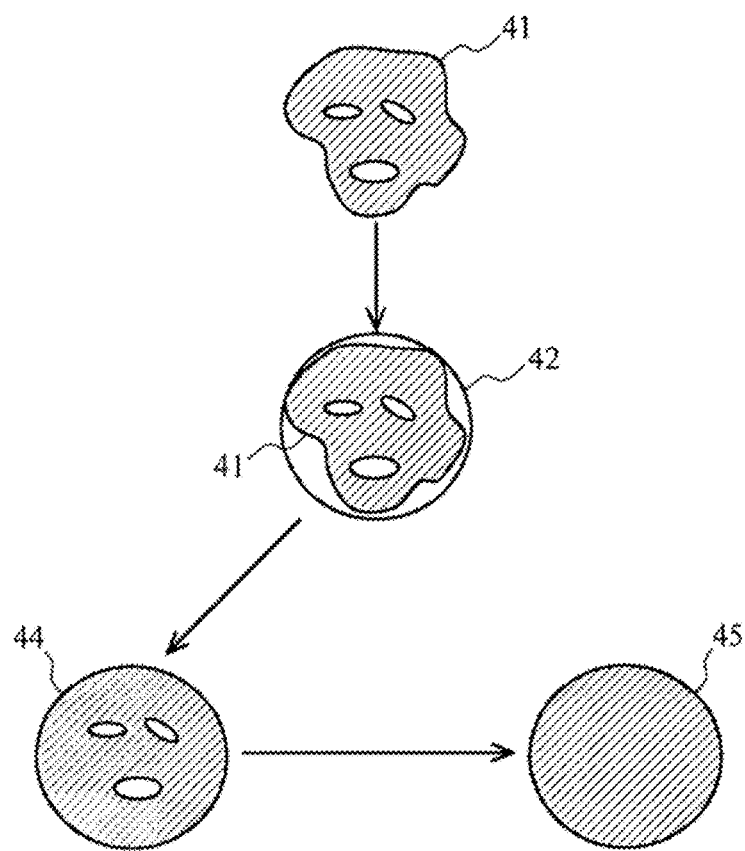

$x_i = sROI(i)$ ⋯ (2)

$y_i = \beta 0 + \beta 1 \times x_i$ ⋯ (3)

$$\begin{bmatrix} y1 \\ y2 \\ \cdot \\ yn \end{bmatrix} = \begin{bmatrix} \beta 0 \\ \beta 0 \\ \cdot \\ \beta 0 \end{bmatrix} + \begin{bmatrix} \beta 1 x1 \\ \beta 1 x2 \\ \cdot \\ \beta 1 xn \end{bmatrix} = \begin{bmatrix} 1 & x1 \\ 1 & x2 \\ & \cdot \\ 1 & xn \end{bmatrix} \begin{bmatrix} \beta 0 \\ \beta 1 \end{bmatrix} \cdots (4)$$

$$Y = X \times B \cdots (5)$$

$x_i = sROI(i)$ ⋯ (2)

$y_i' = R(i)'$ ⋯ (7)

$y_i' = y_i - (\beta 0 + \beta 1 \times x_i)$ ⋯ (8)

$$\begin{bmatrix} y1' \\ y2' \\ \cdot \\ yn' \end{bmatrix} = \begin{bmatrix} y1 \\ y2 \\ \cdot \\ yn \end{bmatrix} - \begin{bmatrix} 1 & x1 \\ 1 & x2 \\ & \cdot \\ 1 & xn \end{bmatrix} \begin{bmatrix} \beta 0 \\ \beta 1 \end{bmatrix} \cdots (9)$$

PULSE WAVE DETECTION DEVICE, VEHICLE DEVICE, AND PULSE WAVE DETECTION PROGRAM

TECHNICAL FIELD

The present invention relates to a pulse wave detection device, a vehicle device, and a pulse wave detection program and relates to a method for detecting the pulse rate of a subject.

BACKGROUND ART

Detection of a pulse wave is important in order to grasp the health state or physiological state of a subject. Usually, a device is attached to a subject for detection of the pulse wave, but there is a high demand for simpler detection methods, and the art for detecting the pulse wave of a subject in a non-contact manner has been keenly studied.

As a result, traffic safety can be further promoted by monitoring pulse wave of a vehicle driver, for example.

The art for detecting the pulse wave in a non-contact manner as mentioned above includes an art in Non-Patent Literature 1. In this art, an arm of the subject is photographed by a camera, and the pulse wave is detected from images from the camera. Since the brightness or color of a body surface is changed by blood flow, the pulse can be detected by image processing of the images.

In the art in Patent Literature 1, when a detection region becomes smaller due to a change in the direction of the face to right or left, the pulse wave is estimated by changing the detection region to a portion in the face where the detection region can be taken relatively widely.

When the pulse wave of the subject is to be detected by a camera, an incident light source is needed, but if environmental lighting is not sufficient, illumination is needed.

If the position of the subject relative to the lighting is constant, the pulse wave can be detected, but if the subject moves, the brightness of the light reflected by the subject is greatly influenced, and the pulse wave cannot be measured anymore, which is a problem.

CITATION LIST

Patent Literature

Patent Literature 1: Japanese Patent Application Publication No. 2014-198201

Non-Patent Literature

Non-Patent Literature 1: "Non-contact Monitoring Techniques—Principles and Applications," D. Teichmann, C. Bruser, B. Eilebrecht, A. Abbas, N. Blanik, and S. Leonhardt, Proc. IEEE Eng., Med. Biol. Soc. 34th Ann. Int. Conf., San Diego, Calif., USA, 2012, pp. 1302-1305.

DISCLOSURE OF INVENTION

Problem to be Solved by the Invention

The object of the present invention is to appropriately detect a pulse wave even if the brightness of a subject changes due to movement of the subject with respect to the lighting.

SUMMARY OF THE INVENTION(S)

(1) The invention described in claim 1 provides a pulse wave detection device, comprising: a video obtainment means for obtaining videos obtained by photographing a body surface of a subject; a region obtainment means for obtaining a region where the body surface is photographed from the obtained videos; a brightness obtainment means for obtaining brightness of the obtained region; a correction means for correcting the obtained brightness by using correlation between a relative rearward and forward position of the body surface and the brightness of the region; and a pulse wave obtainment means for obtaining a pulse wave of the subject on the basis of a change in the corrected brightness of the region.

(2) The invention described in claim 2 provides the pulse wave detection device according to claim 1, wherein the body surface is a face, and the region obtainment means obtains a face region as the region.

(3) The invention described in claim 3 provides the pulse wave detection device according to claim 2, comprising: an illumination means for illuminating the face with infrared light; and a video photographing means for photographing a video of the face illuminated by the infrared light, wherein the video obtainment means obtains the videos from the video photographing means.

(4) The invention described in claim 4 provides the pulse wave detection device according to claim 2 or 3, wherein the correction means obtains the rearward and forward position of the face from the size of the face region.

(5) The invention described in claim 5 provides the pulse wave detection device according to claim 2, 3 or 4, comprising: a face detection region obtainment means for obtaining a face detection region larger than the face including the face, wherein the region obtainment means obtains the face region by using the brightness distribution in the obtained face detection region.

(6) The invention described in claim 6 provides the pulse wave detection device according to any one of claims 2 to 5, wherein when the obtained face region has a closed region not included in the face region, the correction means includes the closed region when determining the size of the face region.

(7) The invention described in claim 7 provides the pulse wave detection device according to claim 3, comprising: an environmental luminance obtainment means for obtaining environmental luminance; and an activation means for activating lighting by the illumination means and video photography by the video photographing means when the obtained environmental luminance falls below a predetermined value.

(8) The invention described in claim 8 provides the pulse wave detection device according to claim 7, comprising: a second pulse wave obtainment means for obtaining the pulse wave when the environmental luminance is at a predetermined value or more, wherein the activation means activates lighting by the illumination means and photography of videos by the video photographing means after obtainment of the pulse wave by the second pulse wave obtainment means is stopped when the obtained environmental luminance falls below a predetermined value.

(9) The invention described in claim 9 provides a vehicle device comprising: the pulse wave detection device according to any one of claims 1 to 8.

(10) The invention described in claim 10 provides a pulse wave detection program for causing a computer to realize: a video obtainment function for obtaining videos obtained by photographing a body surface of a subject; a region obtainment function for obtaining a region where the body surface is photographed from the obtained videos; a brightness obtainment function for obtaining brightness of the obtained region; a correction function for correcting the obtained brightness by using correlation between a relative rearward and forward position of the body surface and the brightness of the region; and a pulse wave obtainment function for obtaining a pulse wave of the subject on the basis of a change in the corrected brightness of the region.

EFFECT OF THE INVENTION(S)

According to the present invention, the pulse wave can be detected appropriately by correcting brightness in accordance with the position of the subject.

BRIEF DESCRIPTION OF DRAWINGS

FIG. 6 is a diagram for supplementary explanation of the flowchart.

FIG. 7 is a diagram for explaining a calculation method for a relational expression between R and sROI.

FIG. 8 is a diagram for explaining a correction expression for R.

BEST MODE(S) FOR CARRYING OUT THE INVENTION

(1) Outline of Embodiment

Figure 1:
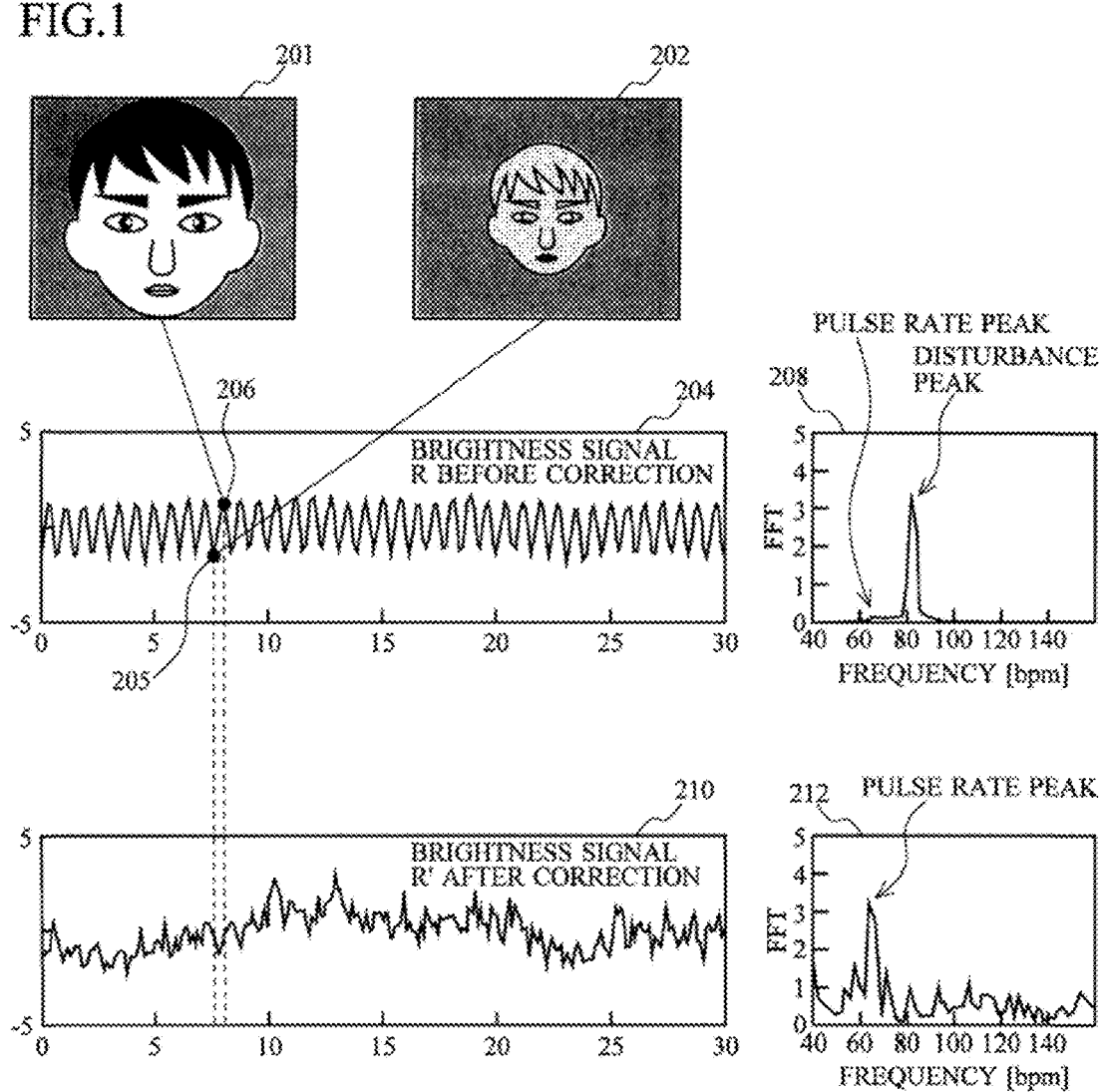
FIG. 1 is a diagram for explaining an outline of this embodiment.

FIG. 1 is a diagram for explaining an outline of this embodiment.

A frame image 201 illustrates one frame image of a video taken by illuminating the face of a subject (a driver seated in the driver's seat of a vehicle, for example) for pulse wave detection using lighting by infrared light emanating from a device installed in front of the driver's seat and by photographing the driver with an infrared camera.

A frame image 202 illustrates a frame image photographed when the subject moves the head part rearward.

Since the face photographed in the frame image 202 moves away from the lighting device, brightness becomes lower than that of the face photographed in the frame image 201, and since the face also moves away from the camera, the size of the face also reduces.

Graph 204 illustrates the temporal change in brightness signal R before correction of the face photographed in videos.

At a point in time 205, the brightness is detected from the frame image 202, and at a point in time 206, the brightness is detected from the frame image 201.

Since the pulse of the subject appears in the change in the brightness of a body surface, the frequency of the pulse can be obtained from the peak of a frequency component by calculating the frequency component by Fourier transform of the brightness signal R by FFT (Fast Fourier Transform) or the like.

However, in the case of graph 204, since the subject's head part is rearward at point in time 205 relative to point in time 206 during detection of the brightness, constancy of brightness of the face surface part is lost, and when the resulting signal is subjected to Fourier transform, the pulse rate peak is buried in noise as illustrated in graph 208, and a disturbance peak caused by forward-and-rearward movement of the face is detected.

In graph 208, a vertical axis indicates a level of the frequency component determined by FFT, and a horizontal axis indicates the frequency in the bpm (beat per minute) unit.

When the face gets closer to the combined camera and lighting device, the brightness increases, and the area of the face increases, while to the contrary, when the face is separated far from the combined camera and lighting device, the brightness decreases, and the area of the face also decreases.

Since the brightness and the face size are correlated, a pulse wave detection device 1 (FIG. 2) which will be described later detects the face from the frame image and corrects the brightness of the face in accordance with the size of the face.

The brightness of the face depends on the distance between the lighting and the face, and the size of the face depends on the distance between the camera and the face, so indirect measurement of the distance from the combined camera and lighting device to the face can be done by determining the size of the face.

Graph 210 illustrates a brightness signal R' after correction in which the brightness is corrected using the size of the face. Correspondence in time to the graph 204 is indicated by two broken lines.

When the brightness signal R' after the correction is converted to a frequency region, the pulse rate peak can be clearly observed as illustrated in graph 212.

As described above, after correction of the brightness of the face photographed on the frame image using the size of the face, by making use of the correlation between the size of the face of the subject in the frame image and the change in its brightness, the pulse wave detection device 1 estimates/measures the pulse rate of the subject from the brightness signal after the correction.

(2) Details of the Embodiment

Figure 2:
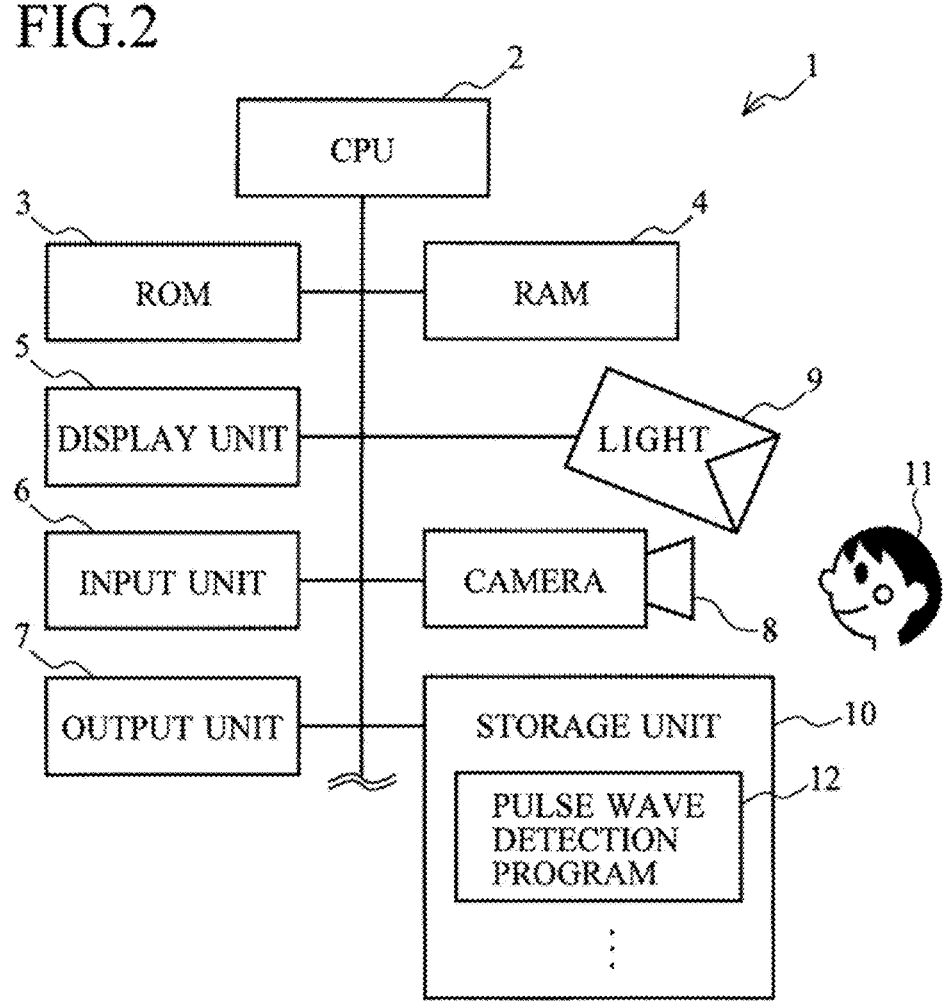
FIG. 2 is a diagram illustrating a configuration of a pulse wave detection device.

FIG. 2 is a diagram illustrating a configuration of a pulse wave detection device 1 of this embodiment.

The pulse wave detection device 1 is mounted on a vehicle, monitors a pulse wave of an occupant (such as a driver and an occupant on a seat next to the driver) and grasps a physiological state such as a body condition and a tension state of the driver and the like, for example.

It can also be used for detecting/monitoring the pulse wave of a patient or a victim at a medical site or a disaster site.

The pulse wave detection device 1 is composed of a CPU (Central Processing Unit) 2, a ROM (Read Only Memory) 3, a RAM (Random Access Memory) 4, a display unit 5, an input unit 6, an output unit 7, a camera 8, a light 9, a storage unit 10 and the like and detects (or estimates) the pulse wave of a subject 11 (a user of the pulse wave detection device 1 and a subject of pulse wave detection).

The CPU 2 is a central processing unit for performing various types of information processing and controls in accordance with a program stored in the storage unit 10, the ROM 3 and the like.

In this embodiment, the video taken by the camera 8 is image-processed, and the pulse wave of the subject 11 is expressed as the pulse rate.

The ROM 3 is a read only memory and stores a basic program, parameters and the like for operation of the pulse wave detection device 1.

The RAM 4 is a memory capable of being read/written and provides a working memory when the CPU 2 is operated.

In this embodiment, the RAM 4 supports the CPU 2 to detect the pulse wave from a skin portion of the frame image by extending and storing a frame image (one still frame of a video) and by storing the calculation result.

The skin portion may be any portion such as the face and limbs as long as the body surface is exposed, but in this embodiment, the pulse wave is detected from the surface of the face (face surface) as an example.

The display unit 5 is constituted by using a display device such as a liquid crystal screen and displays information required for operation of the pulse wave detection device 1 such as an operation screen of the pulse wave detection device 1 and display of the pulse rate.

The input unit 6 is constituted by using an input device such as a touch panel overlaying the display device and receives input of various types of information from presence/absence of a touch on the screen display.

The output unit 7 is an interface for outputting the various types of information to an external device and can output the detected pulse rate or an alarm when a change appears in the pulse rate, for example.

The output unit 7 can make outputs to other control devices such as a control device for controlling a vehicle. The control device which receives the output of the pulse rate from the output unit 7 can determine sleepiness, the tension state and the like of the driver and perform controls for drivers such as vibrating the steering wheel or seat for waking the driver, outputting an alarm sound and a message and the like. Moreover, as controls for the vehicle, at least any one of inter-vehicle distance control, vehicle speed control and brake control can be performed in accordance with the tension state of the driver determined on the basis of the pulse rate. For example, when the control device determines that the driver is in a high tension state exceeding a predetermined value, it activates control so that inter-vehicle distance is made larger than a reference value, control the vehicle speed so as to fall below a predetermined vehicle speed, and execute deceleration processing or the like by an automatic brake operation if the speed is at or above a predetermined vehicle speed.

The camera 8 is an infrared camera and is constituted by using an optical system constituted by a lens and an infrared image sensor which converts an image formed by that sensor into an electric signal, and is installed so that the vicinity of the face of the subject 11 becomes a photography target.

The camera 8 photographs the subject 11 at a predetermined frame rate and outputs videos constituted by these consecutive frame images (still images).

The frame image is constituted by an array of pixels which are minimum units constituting an image, and each pixel detects the infrared light of a frequency band when irradiated with the light 9.

Since the camera 8 is installed in front of the face of the subject 11, when the subject 11 moves the face forward or rearward, the size of the photographed face is changed.

In more detail, when the subject 11 moves the face forward, the face gets closer to the camera 8, and the size of the face increases, while when the subject 11 moves the face rearward, the face is separated far from the camera 8, and the size of the face decreases.

The light 9 is a lighting device for producing the infrared light in a predetermined frequency band to irradiate the subject, and is installed in front of the face of the subject 11, and illuminates the face of the subject 11 from the front.

When the subject 11 moves the face forward, the face gets closer to the light 9, and the brightness of the infrared light reflected by the face increases, while when the subject 11 moves the face rearward, the face moves away from the light 9, and the brightness of the infrared light reflected by the face decreases.

The camera 8 and the light 9 may be a camera with light in which the camera 8 and the light 9 are integrated.

The pulse wave detection device 1 detects the pulse wave of the subject 11 using infrared light but may use light in other frequency bands such visible light. In this case, the camera 8 and the light 9 are constituted with compatibility corresponding with the light type.

The storage unit 10 is constituted by using a storage medium such as a hard disk and an EEPROM (Electrically Erasable Programmable Read-Only Memory) and stores a pulse wave detection program 12 by which the CPU 2 detects the pulse wave and other programs and data.

Data on the pulse wave detected by the CPU 2 in accordance with the pulse wave detection program 12 is temporarily stored in the RAM 4 and is output to the outside as necessary or is stored in the storage unit 10.

The pulse wave detection program 12 is a program for causing the CPU 2 to execute the pulse wave detection processing.

The CPU 2 performs specification of the skin portion of a user in the videos, correction of the brightness on the basis of the size of the face, and detection of the pulse wave (and subsequently the pulse rate) from the specified skin portion by executing the pulse wave detection program 12.

Hereinafter, the pulse wave detection processing executed by the pulse wave detection device 1 will be described.

Figure 3:
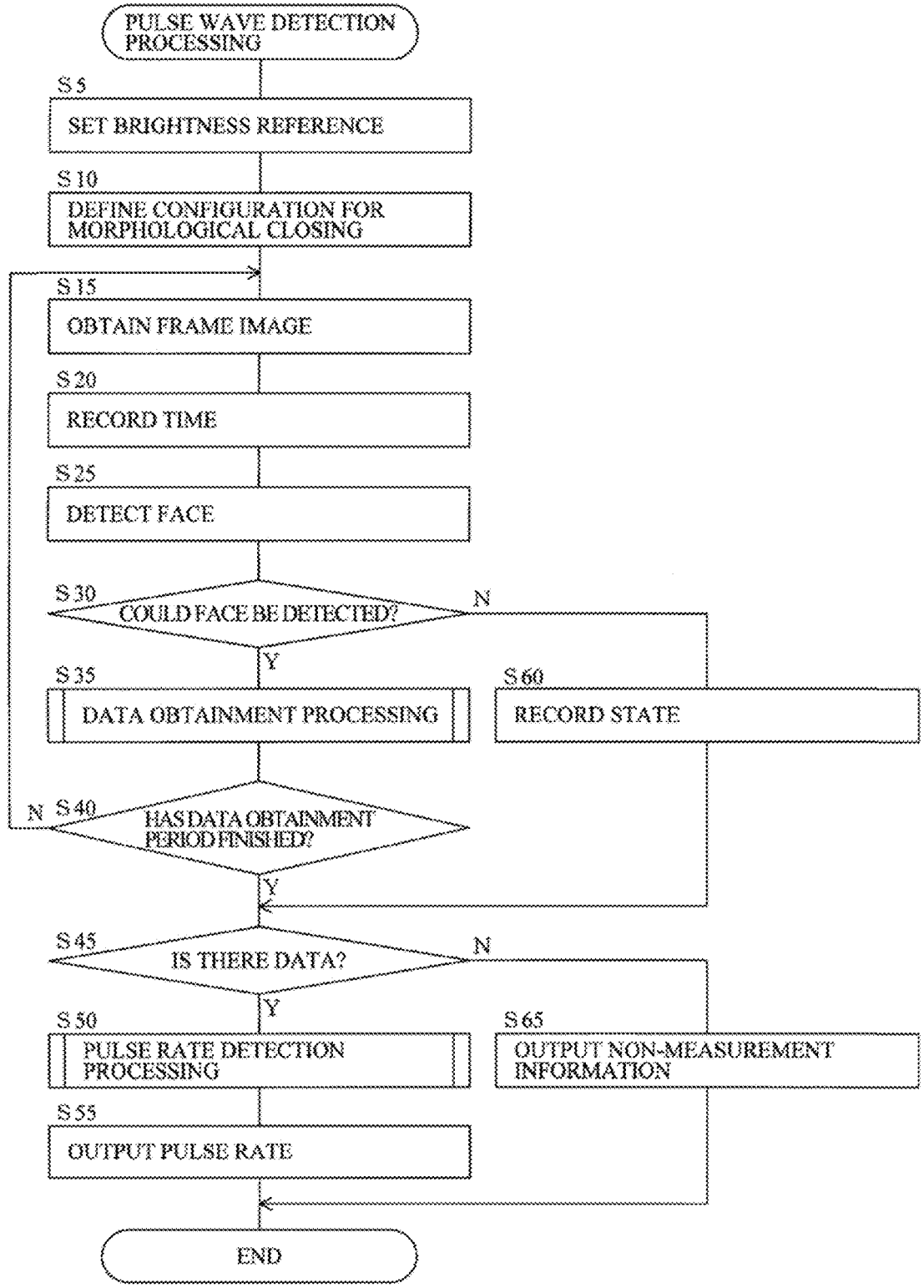
FIG. 3 is a flowchart for explaining a procedure of pulse wave detection processing.

FIG. 3 is a flowchart for explaining a procedure of the pulse wave detection processing executed by the pulse wave detection device 1.

The following processing is executed by the CPU 2 in accordance with the pulse wave detection program 12.

First, the CPU 2 sets a brightness reference by storing a lowest brightness reference and a highest brightness reference in the RAM 4 (Step 5).

The pulse wave detection device 1 measures the brightness in steps from 0 (lowest brightness) to 255 (highest brightness), for example, but here, the lowest brightness reference is assumed to be set at 105 and the highest brightness reference at 255 as an example.

The lowest brightness reference and the highest brightness reference are references to be used when a pixel corresponding to the body surface from the frame image is to be identified, and an optimal value is set by the pulse wave detection program 12 in advance as a parameter.

By using the brightness references suitable for detection of the brightness of the face, detection accuracy of the brightness of the face can be improved.

The CPU 2 defines the configuration of a morphological closing element by storing the parameter defining the configuration for the morphological closing element in the RAM 4 (Step 10).

As will be described later, when a region with pixels of a brightness between that of the lowest brightness reference and the highest brightness reference is detected as a face region, it becomes a distorted shape in general.

To change this shape into one suitable for pulse wave detection or the detection of the size of the face morphological closing is used.

The CPU 2 drives the light 9 in order to illuminate the face of the subject 11 and drives the camera 8 so as to take videos of the face of the subject 11 and to start detection of the pulse wave.

As described above, the pulse wave detection device 1 includes illumination means for illuminating the face with infrared light and video photographing means for photographing videos of the face illuminated with the infrared light.

The CPU 2 obtains a frame image from video data photographed by the camera 8 and stores it in the RAM 4 (Step 15).

As described above, the pulse wave detection device 1 includes video obtainment means for obtaining videos taken by photographing the body surface (the face, here, as an example) of the subject 11.

Then, the video obtainment means obtains videos from the video photographing means (camera 8).

The CPU 2 records the time (time and date) when the frame image is obtained in the RAM 4 (Step 20).

This time defines the time on a time axis for Fourier analysis of the brightness later.

When the image obtainment time is recorded with the frame image, this may be used, or the time measured by the CPU 2 by using its own clock may be used.

The CPU 2 detects the face in the frame image stored in the RAM 4 and stores the position and size of the detected face in the RAM 4 (Step 25).

In more detail, as illustrated in a frame image 31 in FIG. 6, the CPU 2 detects the face, as shown by rectangle 32. As for the face detection algorithm, an algorithm used in general in the art of face detection is used.

Returning to FIG. 3, subsequently, the CPU 2 determines whether the face could be detected or not (Step 30).

If the face could be detected (Step 30; Y), the CPU 2 executes data obtainment processing, which will be described later, for obtaining data required for detection of the pulse wave (Step 35).

However, if the face could not be detected (Step 30; N), the CPU 2 records a state where the face could not be detected by setting a flag indicating that the face could not be detected at the RAM 4 or the like, for example (Step 60).

The CPU 2 executes the data obtainment processing, and then determines whether the data obtainment period for obtaining the data has finished or not (Step 40).

If the data obtainment period has not yet finished (Step 40; N), the CPU 2 returns to Step 15 and executes similar processing for the subsequent frame image.

On the other hand, when the data obtainment period has finished (Step 40; Y), the CPU 2 transfers to processing at Step 45.

The data obtainment period is a specified period of time for the construction of videos used for the pulse wave detection, and in this embodiment, the pulse wave is detected from videos of duration 30 seconds as an example.

After the data obtainment period is finished (Step 40; Y) or after a state where the face could not be detected is recorded (Step 60), the CPU 2 accesses the RAM 4 and determines whether there is data obtained at Step 35 (Step 45).

In more detail, the CPU 2 accesses the RAM 4 and makes the determination by checking whether there is a brightness signal obtained at Step 35.

If there is no data in the RAM 4 (Step 45; N), this means the face could not be detected at Step 30, and the CPU 2 reads the record for the state where the face could not be detected from the RAM 4, creates non-measurement indication (an indication that the measurement failed), outputs it to the display unit 5 and the output unit 7 (Step 65), and the processing is finished.

On the other hand, if there is data in the RAM 4 (Step 45; Y), the CPU 2 corrects the brightness signal R due to a relative rearward and forward position of the face by using the obtained data and then, executes the pulse rate detection processing for detecting the pulse rate by using the brightness signal R' after the correction and stores the detected pulse rate in the RAM 4 as will be described later (Step 50).

The relative rearward and forward positions of the face refer to rearward and forward positions of the face relative to the position of the face obtained from one frame image as a reference. These relative rearward and forward positions are acquired from the size of BlobFill 45 (which will be described later) obtained from each of the frame images.

The CPU 2 outputs the pulse rate stored in the RAM 4 to the display unit 5 and the output unit 7 (Step 55) and finishes the processing.

As described above, the pulse wave detection device 1 includes a correction means for correcting the brightness obtained earlier by using correlation between the brightness at the relative rearward and forward positions of the body surface (face) and in the region where the body surface is photographed, and pulse wave obtainment means for obtaining the pulse wave of the subject 11 on the basis of the change in the corrected brightness of the region.

Figure 4:
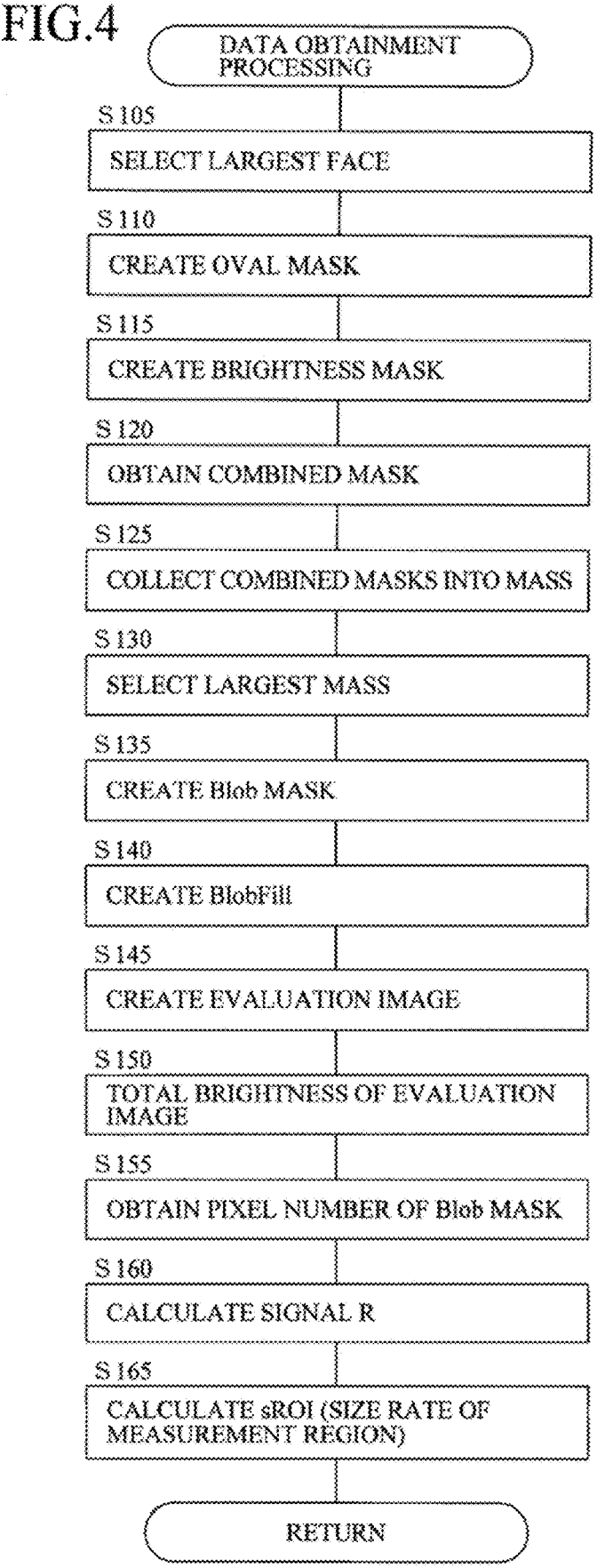
FIG. 4 is a flowchart for explaining a procedure of data obtainment processing.

FIG. 4 is a flowchart for explaining the procedure of the data obtainment processing illustrated at Step 35 in FIG. 3.

First, the CPU 2 selects the largest face from the faces detected at Step 25 in FIG. 3 and stores the selected result (that is, information identifying the selected face from the other faces) in the RAM 4 (Step 105).

This is done to select the face of the subject 11 (the largest since it is positioned in front of the camera 8) if there was a third party around the subject 11, and the face of the third party was also recognized.

Particularly when the pulse wave detection device 1 is used for a driver of a vehicle, since the face of a person seated on the driver's seat appears largest in the image, the face of the driver can be selected by this process.

The CPU 2 creates an oval mask for the selected face and stores data specifying the oval mask in the RAM 4 (Step 110).

The data specifying the oval mask is configured by parameters such as a shape of the oval mask, a coordinate value specifying a position of the oval mask in the frame image and the like.

In the following, such processing will be abbreviated such that the oval mask is stored in the RAM 4 and the like.

A frame image 35 in FIG. 6 illustrates that an oval mask 36 is created for the face of the subject 11 indicated by a rectangle 32.

As described above, the CPU 2 sets the oval mask 36 by defining an oval region to include the face so that the face of the subject 11 is contained inside.

In this embodiment, the oval mask is used as an example, but a mask with another shape such as a rectangle can also be used.

The CPU 2 specifies the face region inside the set oval mask 36 and detects the pulse wave from the brightness of the region. The inventor of this application has found as the result of trial and error that the pulse wave detection can be favorably performed by limiting the region for detecting the pulse wave by this oval mask 36.

As described above, the pulse wave detection device 1 includes a face detection region obtainment means for obtaining a face detection region (such as an oval mask) and including a region larger than the face.

Returning to FIG. 4, subsequently, the CPU 2 creates a brightness mask from the frame image and stores it in the RAM 4 (Step 115).

The brightness mask is a region configured by pixels in the frame image whose pixel brightness is between the lowest brightness reference and the highest brightness reference, and the CPU 2 creates the brightness mask by examining the brightness of each pixel of the frame image.

The CPU 2 creates a combined mask by combining the oval mask and the brightness mask stored in the RAM 4 and stores the combined mask in the RAM 4 (Step 120).

The combined mask is a portion included in the oval mask in the brightness mask, and the CPU 2 takes a logical product of the oval mask and the brightness mask and creates the combined mask by the pixels whose values are true.

The CPU 2 collects the combined masks into a mass (Step 125), selects the largest mass in the collected masses and stores the largest mass as a new combined mask in the RAM 4 (Step 130).

There are cases where a divided face is photographed or another object is photographed in the position of the oval mask, for example. That is, there are cases where a part of the ear or forehead is photographed as being divided by hair with respect to the center part of the face, and the hand is photographed at slight distance away. In such cases, the center part of the face, the ear, the forehead, the hand and the like are recognized as separate combined masks.

A group of the combined masks with distances between peripheral edges of each of the combined masks at a predetermined threshold value or less are collected into a mass in order to handle them as one combined mask (Step 125).

On the other hand, the largest mass is selected in order to exclude the mass of the combined mask of the hand present at a position slightly away from the face and to use the mass of the combined mask of the face (Step 130).

As described above, the CPU 2 collects the combined masks into a mass of each portion such as a face and a hand by grouping the combined masks into masses and since the largest mass is likely to be the face, the largest combined mask is selected.

The pulse wave can also be detected from the body surface of the hand or the like, but since the pulse wave detection device 1 corrects the brightness by indirectly measuring the distance between the light and the face according to the size of the face, if other portions are included with the face, the size of the face becomes larger than its actual size, and this makes the brightness correction difficult.

Thus, such problem can be avoided by selecting the largest combined mask.

The CPU 2 creates a Blob mask from the largest combined mask stored in the RAM 4, stores it in the RAM 4 (Step 135) and further creates BlobFill from the Blob mask and also stores this in the RAM 4 (Step 140).

Details regarding the Blob mask and the filled blob mask BlobFill are as follows.

The combined mask 41 illustrated in FIG. 6 is the largest combined mask stored by the CPU 2 in the RAM 4 at Step 130. In general, the combined mask has an irregular shape.

The CPU 2 reads out the parameter defining the configuration for the morphological closing element stored at Step 10 (FIG. 3) from the RAM 4, shapes the combined mask 41 into a smooth shape 42 so as to create the Blob mask 44, which is suitable for pulse wave detection. The CPU 2 uses the Blob mask 44 for detection of the pulse wave.

In the case of the Blob mask 44, a closed region not included in the Blob mask 44 might be formed in the portions such as the eyes and the mouth.

Since these closed regions are included in an area of the face, the CPU 2 creates BlobFill 45 including these closed regions in the mask and uses it for determination of the size of the face.

The CPU 2 uses the Blob mask 44 for detection of the pulse wave and uses BlobFill 45 for estimation of the size of the face.

As described above, the correction means included in the pulse wave detection device 1 uses BlobFill, which includes the closed regions within the face region, when the face region has a closed region not included in Blob mask 44.

Returning to FIG. 4, the CPU 2 creates the Blob mask (Step 135) and BlobFill (Step 140), and then creates an evaluation image and stores it in the RAM 4 (Step 145).

The evaluation image is a portion of the image used for detection of the pulse wave in the frame image, and the CPU 2 creates the evaluation image by extracting a region corresponding to the Blob mask 44 from the frame image.

More specifically, the CPU 2 takes out the portion corresponding to the Blob mask from the frame image by calculating the logical product of the Blob mask and the frame image and extracting the pixels of the portion which have values of 'true' so as to create the evaluation image.

In other words, the Blob mask has a role of a cutting die for extracting the evaluation image from the frame image, and the CPU 2 detects the pulse wave from the brightnesses of the pixels comprising the evaluation image.

As described above, the pulse wave detection device 1 includes a region obtainment means for obtaining a region (evaluation image) where the body surface (the face, here) is obtained from the videos and brightness obtainment means for obtaining the brightness of the obtained region.

In addition, the region obtainment means obtains the face region by using the distribution of the brightness in the face detection region (the oval mask).

The CPU 2 totals the values of the brightnesses of pixels comprising the evaluation image stored in the RAM 4, stores the total value of the brightness in the RAM 4 (Step 150), and further obtains the number of pixels in the Blob mask stored in the RAM 4 (Step 155).

The CPU 2 calculates the brightness signal R before the correction by calculating the average value of the brightness of the evaluation image through division of the total value of the brightness stored in the RAM 4 by the number of pixels in the Blob mask stored in the RAM 4 and stores it in the RAM 4 (Step 160).

The CPU 2 calculates sROI (size of Region of Interest), stores it in the RAM 4 (Step 165) and returns to the main routine.

The sROI is the ratio of a measurement region (size of the face) to the frame image, and the CPU 2 calculates sROI by dividing the number of pixels in BlobFill by the number of pixels in the frame image.

The sROI indicates a ratio of the size of the face in the frame image by % and indicates a rearward and forward position of the face of the subject 11 (the larger the sROI is, the shorter the distance between the light 9 and the face is).

As will be described later, the CPU 2 corrects the brightness signal R before the correction by the value of sROI and generates the brightness signal R' after the correction.

As described above, the correction means obtains the rearward and forward position of the face by the size of the face region.

The sROI is the ratio of the measurement region to the frame image, but since the number of pixels in the frame image is fixed, the number of pixels in the evaluation image can be made sROI.

Figure 5:
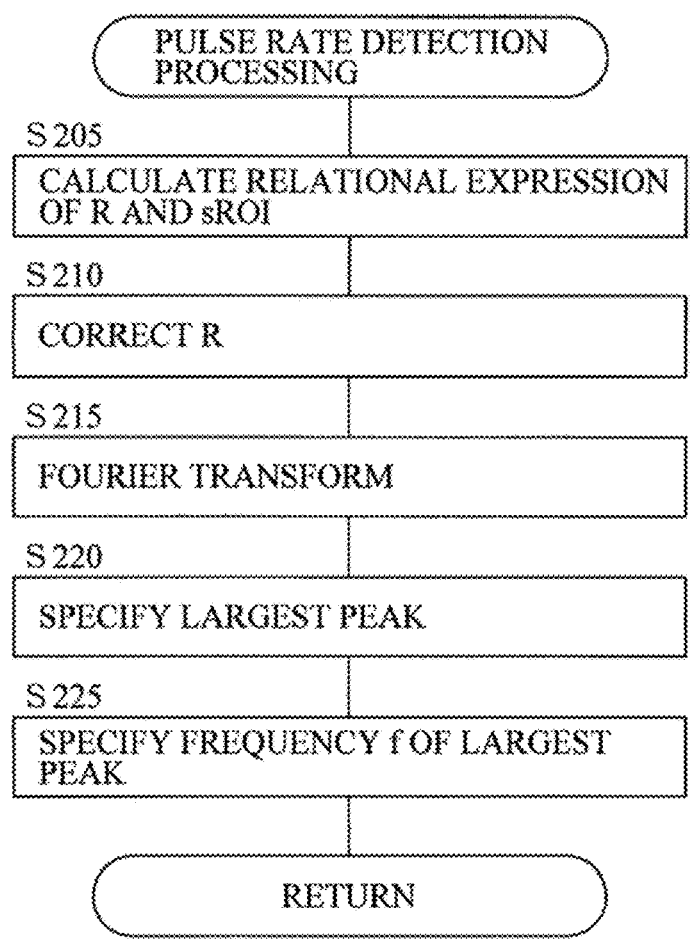
FIG. 5 is a flowchart for explaining a procedure of pulse rate detection processing.

FIG. 5 is a flowchart for explaining the procedure of the pulse rate detection process illustrated at Step 50 in FIG. 3.

First, the CPU 2 reads out the brightness signal R before the correction and sROI obtained during the data obtainment period (30 seconds) from the RAM 4.

Then, the CPU 2 calculates the relational expression between the brightness signal R and sROI by using the least-squares method as will be described later, and stores it in the RAM 4 (Step 205).

Subsequently, the CPU 2 calculates the brightness signal R' after the correction by correcting the brightness signal R by applying sROI to the relational expression and stores the brightness signal R' in the RAM 4 (Step 210).

Then, the CPU 2 calculates the frequency component of the brightness signal R' by subjecting the brightness signal R' to the Fourier transform and stores this in the RAM 4 (Step 215).

Next, the CPU 2 determines the maximum peak in the frequency component of the brightness signal R' stored in the RAM 4 (Step 220).

Then, the CPU 2 determines the frequency f of the maximum peak, stores it as the pulse rate of the subject 11 in the RAM 4 (Step 225), and returns to the main routine.

FIG. 7 is a diagram for explaining the calculation method of the relational expression between the brightness signal R and sROI according to Step 205 in FIG. 5.

The RAM 4 stores the brightness signals R for 30 seconds, and they are assumed to be R(0), R(1), ..., R(i) ... in increasing time order.

Similarly, sROI stored in the RAM 4 is also assumed to be sROI(0), sROI(1), sROI(2), ..., sROI(i), ... in increasing time order.

Since the brightness signal R(i) and the sROI(i) are obtained from the same frame image, they correspond to each other in time and have values at the same time.

Here, by assuming that a linear relation of $yi=\beta 0+\beta 1 \times xi$ illustrated in expression (3) is completed with yi=R(i), xi=sROI(i) as illustrated in expression (1) and expression (2), an expression (4) is completed. The expression (4) presents a matrix representation of the least-squares method in order to acquire $\beta 0$ and $\beta 1$, which are required.

Assuming that Y=X×B in expression (4), as in an expression (5), B can be solved by an expression (6). A letter "T" and numeral "−1" expressed by superscript characters in the expression mean a transposed matrix and an inverse matrix, respectively.

The CPU 2 calculates $\beta 0$ and $\beta 1$ by generating X and Y from the brightness signal R and sROI stored in the RAM 4 and by evaluating the expression (6). As a result, the relational expression $yi=\beta 0+\beta 1 \times xi$ between the brightness signal R and sROI is determined.

FIG. 8 is a diagram for explaining the correction expression for the brightness signal R according to Step 210 in FIG. 5.

Reference characters yi and xi are the same as those in FIG. 7. Here, as illustrated in expression (7), by representing R(0)', R(1)', ..., R(i)', ... which are the brightness signals after the correction by yi', expression (8) is completed, and this is the correction expression for the brightness signal R. When this is expressed in a matrix, it becomes expression (9), and when yi and xi are substituted in that, yi', that is, the brightness signal R' after the correction, can be calculated.

Figure 9:
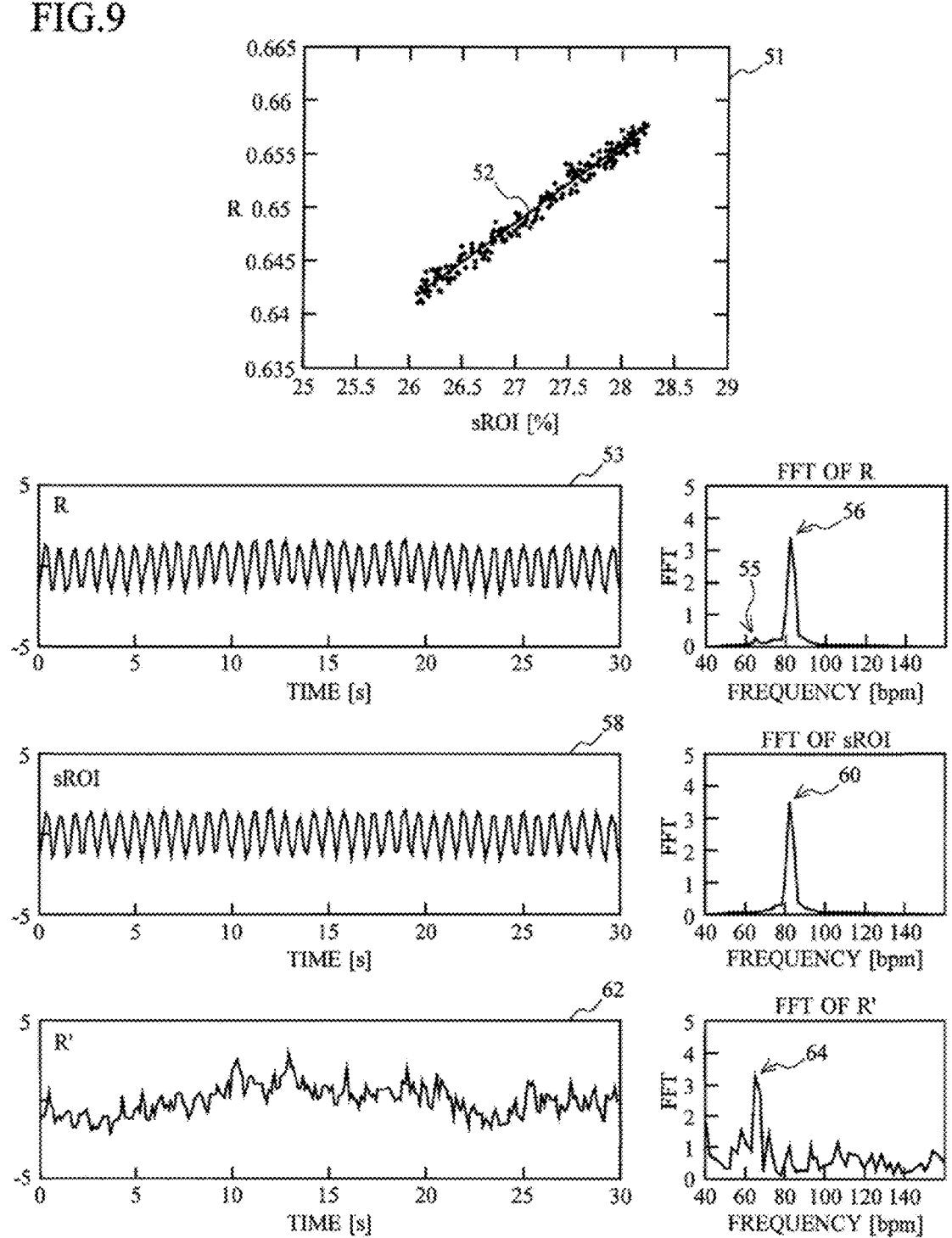
FIG. 9 is a diagram for explaining a correction experiment for R.

FIG. 9 is a diagram for explaining a correction experiment for the brightness signal R.

This experiment was conducted such that the subject 11 is positioned indoors in a dark environment, and the pulse wave of the subject 11 was detected by the pulse wave detection device 1.

As a result, an effect of the correction when an arbitrary back-and-forth oscillation is applied to the position of subject 11 can be verified.

Scatter diagram 51 is a diagram in which, with an x-axis (horizontal axis) for sROI and a y-axis (vertical axis) for the brightness signal R, (xi, yi) is plotted.

Straight line 52 (regression line) fitted to these data by linear approximation according to expression (3) specifies the relational expression between R and sROI, and the y-intercept of the straight line 52 is $\beta 0$, and the inclination is $\beta 1$.

Graph 53 represents a temporal change in the brightness signal R over 30 seconds. When this is subjected to Fourier transform using an FFT, a disturbance peak 56 due to the rearward and forward movement of the face appears in the vicinity of 80 [bpm], and a pulse rate peak 55 which appears in the vicinity of 65 [bpm] is buried in noise.

Graph 58 represents the temporal change in sROI in over 30 seconds. When this is subjected to Fourier transform, the disturbance peak 60 by the rearward and forward movement of the face appears in the vicinity of 80 [bpm].

Graph 62 represents a temporal change of the brightness signal R' after the correction in 30 seconds. When this is subjected to Fourier transform, a pulse rate peak 64 clearly appears in the vicinity of 65 [bpm].

As described above, when the brightness signal R is corrected using the sROI, the pulse rate signal buried in the disturbance can be extracted from the disturbance.

Figure 10:
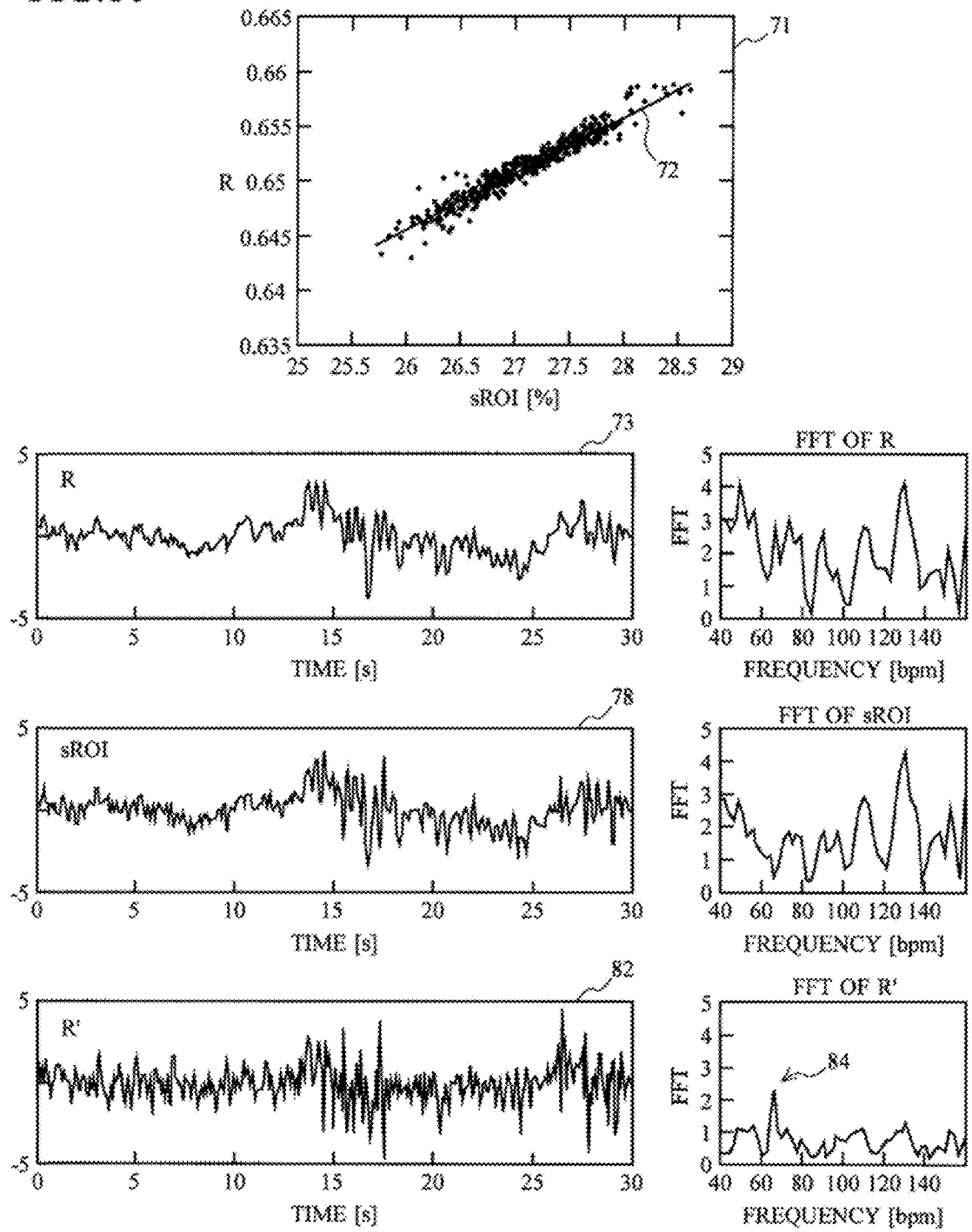
FIG. 10 is a diagram for explaining a correction experiment for R.

FIG. 10 is a diagram for explaining another correction experiment for the brightness signal R.

This experiment was conducted such that the subject 11 is positioned in a darkened vehicle, and the pulse wave of the subject 11 was detected by the pulse wave detection device 1 while the vehicle was being driven.

As a result, an effect of the correction when vibration is applied from the outside to the subject 11 can be verified.

Scatter diagram 71 is a diagram in which, with the x-axis (horizontal axis) for sROI and the y-axis (vertical axis) for R, yi is plotted against xi.

Straight line 72 fitted to these of data by linear approximation according to expression (3) specifies the relational expression between R and sROI, and the y-intercept of the straight line 72 is $\beta 0$, and the inclination is $\beta 1$.

Graph 73 represents a temporal change in the brightness signal R over 30 seconds. Since the vehicle rocks, the signal is more irregular and disorderly than that in graph 53 in the previous experiment. When this signal is subjected to Fourier transform by FFT, peaks appear at various frequencies.

Graph 78 represents a temporal change in sROI over 30 seconds. Since the subject 11 rocks due to vehicle motion, the signal is more irregular and disorderly than that in graph 58. When this signal is subjected to Fourier transform by FFT, peaks appear at various frequencies.

Graph 82 represents the temporal change in the brightness signal R' after the correction over 30 seconds. When this signal is subjected to Fourier transform, the pulse rate peak 84 clearly appears in the vicinity of 65 [bpm].

As described above, even if the subject 11 rocks due to vehicle motion, when the brightness signal R is corrected using sROI, the pulse rate signal buried in the disturbance can be extracted from the disturbance.

Figure 11:
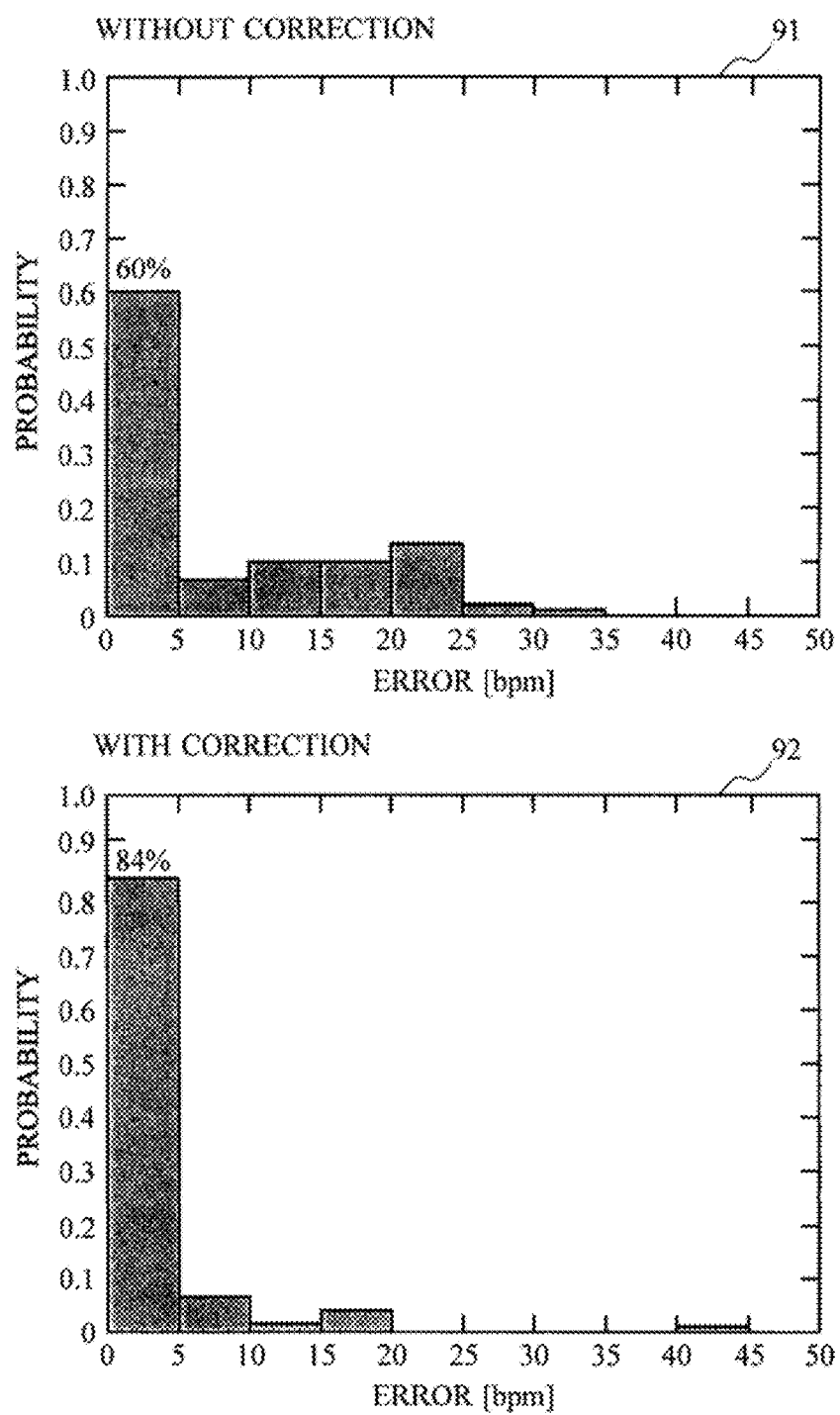
FIG. 11 is a diagram for explaining an experiment result from measurement of an error rate.

FIG. 11 is a diagram for explaining the experiment result for which the error rate for the pulse wave detection device 1 was measured.

The experiment was conducted in the darkened cabin of a vehicle in motion, and the measurement data consisted of 111 videos, each of length 30 seconds.

In this experiment, the pulse rate of subject 11 was detected by the pulse wave detection device 1, and it was also measured accurately by another device at the same time, and the probability (rate) of the error in pulse rate determined by the pulse wave detection device 1 being less than or equal to 5 [bpm], greater than 5 [bpm] and less than or equal to 10 [bpm], etc, is expressed by a histogram.

Graph 91 represents a case without correction of the brightness signal R, and graph 92 represents a case with correction of R.

As illustrated in graph 91, when the brightness signal R is not corrected, the 0 to 5 [bpm] bin (containing measurements with the highest accuracy) contains 60% of measurements, but when the brightness signal R is corrected this bin reaches 84%, as illustrated in graph 92.

According to this experiment result, it can be seen that the art of correcting the brightness in accordance with the size of the face is extremely effective.

(Variation)

In this variation, a vehicle device in which the pulse wave detection device 1 is mounted will be described.

In an environment where infrared light due to natural light exists, this light becomes a disturbance and so the described pulse wave detection device 1 is most suitable for operation at night.

Thus, the vehicle device detects the pulse wave of the driver by activating the pulse wave detection device 1 when environmental luminance outside the vehicle falls below a predetermined reference value.

In this case, the vehicle device includes an environmental luminance obtainment means for obtaining the environmental luminance and an activation means for starting lighting by illumination means and photographing of videos by video photographing means when the environmental luminance falls below the predetermined value.

The vehicle device can have a second pulse wave detection device for detecting a pulse wave by natural light mounted as in the pulse wave detection device proposed by the applicant of this application in Japanese Patent Application Publication No. 2016-193022, for example.

In this case, when the environmental luminance outside the vehicle falls below the predetermined reference value, the vehicle device switches detection of the pulse wave from the second pulse wave detection device to the pulse wave detection device 1.

In this case, the vehicle device includes a second pulse wave obtainment means for obtaining the pulse wave when the environmental luminance is at the predetermined value or more, and when the obtained environmental luminance falls below the predetermined value, and includes the activation means for starting the lighting by the illumination means and photographing of videos by the video photographing means after obtainment of the pulse wave by the second pulse wave obtainment means is stopped.

As described above, the pulse wave detection device 1 can detect the pulse rate buried in the disturbance due to the rearward and forward movement of the face by correcting the brightness change of the measurement region (face) in accordance with the relation of the brightness to the rearward and forward position (size of the face region) of the face acquired in advance and by estimating the pulse on the basis of the corrected brightness change.

As a result, even if the rearward and forward position of the face is changed, high detection accuracy of the pulse wave can be realized.

REFERENCE SIGNS LIST

1 Pulse wave detection device
2 CPU
3 ROM
4 RAM
5 Display unit
6 Input unit
7 Output unit
8 Camera
9 Light
10 Storage unit
11 Subject
12 Pulse wave detection program
31, 35 Frame image
32 Rectangle
36 Oval mask
41 Combined mask
42 Shape
44 Blob mask
45 BlobFill
51 Scatter diagram
52 Straight line
53, 58, 62 Graph
55, 64 Pulse rate peak
56, 60 Disturbance peak
71 Scatter diagram
72 Straight line
73, 78, 82 Graph
84 Pulse rate peak
91, 92 Graph
201, 202 Frame image
204, 208, 210, 212 Graph
205, 206 Point in time

The invention claimed is:

1. A pulse wave detection, device comprising:
a processor programmed to:
receive videos obtained by photographing a body surface of a subject;
obtain a region where the body surface is photographed from the received videos;
determine a brightness of the obtained region;
correct the determined brightness by using a correlation between (i) a relative rearward position of the body surface and a relative forward position of the body surface, and (ii) the determined brightness of the region, the relative forward position of the body surface is defined by a same portion body surface of the subject moving forward in the received video relative to the rearward position of the body surface; and detect a pulse wave of the subject based on a change in the corrected brightness of the region.

2. The pulse wave detection device according to claim 1, wherein:

the body surface is a face, and the processor obtains a face region as the region.

3. The pulse wave detection device according to claim 2, further comprising:

a light configured to illuminate the face with infrared light; and a video camera configured to capture a video of the face illuminated by the infrared light, wherein the processor receives the videos from the video camera.

4. The pulse wave detection device according to claim 3, wherein the processor is programmed to:

obtain environmental luminance; and activate lighting by the light and video photography by the video camera when the obtained environmental luminance falls below a predetermined value.

5. The pulse wave detection device according to claim 4, wherein the processor is programmed to:

detect the pulse wave when the environmental luminance is at a predetermined value or more, and activate the lighting by the light and the photography of videos by the video camera after the detecting of the pulse wave is stopped when the obtained environmental luminance falls below the predetermined value.

6. The pulse wave detection device according to claim 2, wherein the processor determines the rearward position and the forward position of the face from a size of the face region.

7. The pulse wave detection device according to claim 2, wherein the processor is programmed to:

determine a face detection region that is larger than the face and includes the face, and obtain the face region by using the brightness distribution in the determined face detection region.

8. The pulse wave detection device according to claim 2, wherein when the determined face region has a closed region not included in the face region, the processor includes the closed region when determining a size of the face region.

9. A vehicle device comprising:

the pulse wave detection device according to claim 1.

10. A non-transitory computer readable storage medium storing a pulse wave detection program, which when executed, causes a computer to perform:

receiving videos obtained by photographing a body surface of a subject;

obtaining a region where the body surface is photographed from the received videos;

determining a brightness of the obtained region;

correcting the determined brightness by using a correlation between (i) a relative rearward position of the body surface and a relative forward position of the body surface, and (ii) the determined brightness of the region, the relative forward position of the body surface is defined by a same portion body surface of the subject moving forward in the received video relative to the rearward position of the body surface; and detecting a pulse wave of the subject based on a change in the corrected brightness of the region.

* * * * *